United States Patent
Chiyama et al.

(10) Patent No.: US 12,059,019 B2
(45) Date of Patent: Aug. 13, 2024

(54) METHOD OF PRODUCING EDIBLE FILM, FILM FORMULATION, AND EDIBLE FILM

(71) Applicant: NISSHA CO., LTD., Kyoto (JP)

(72) Inventors: Masateru Chiyama, Kyoto (JP); Ikuya Takahashi, Kyoto (JP); Mariko Sanada, Kyoto (JP); Hiroyuki Nagai, Kyoto (JP)

(73) Assignee: NISSHA CO., LTD., Kyoto (JP)

( * ) Notice: Subject to any disclaimer, the term of this patent is extended or adjusted under 35 U.S.C. 154(b) by 0 days.

(21) Appl. No.: 17/779,298

(22) PCT Filed: Mar. 25, 2020

(86) PCT No.: PCT/JP2020/013466
§ 371 (c)(1),
(2) Date: May 24, 2022

(87) PCT Pub. No.: WO2021/106240
PCT Pub. Date: Jun. 3, 2021

(65) Prior Publication Data
US 2022/0386676 A1    Dec. 8, 2022

(30) Foreign Application Priority Data
Nov. 29, 2019  (JP) ................. 2019-216138

(51) Int. Cl.
*A23P 10/00* (2016.01)
*A23L 5/00* (2016.01)

(52) U.S. Cl.
CPC ............... *A23P 10/00* (2016.08); *A23L 5/00* (2016.08)

(58) Field of Classification Search
CPC .......... A23P 10/00; A23P 30/20; A23P 30/25; A23P 30/00; A23L 5/00; A61K 9/006;
(Continued)

(56) References Cited

U.S. PATENT DOCUMENTS 5,569,482 A    10/1996  Naga et al.
5,589,218 A *  12/1996  Vassiliou ................. A23P 30/25
                                                        426/573
(Continued)

FOREIGN PATENT DOCUMENTS

CN    102892815 A    1/2013
JP    S5212941 A     1/1977
(Continued)

OTHER PUBLICATIONS

European Patent Office, Extended European Search Report Issued in Application No. 20894217.7, Aug. 16, 2022, Germany, 9 pages.

*Primary Examiner* — Jeffrey P Mornhinweg
(74) *Attorney, Agent, or Firm* — Alleman Hall & Tuttle LLP

(57) ABSTRACT

An edible powder formed of particles smaller than a film thickness, a predetermined component, and an edible liquid having a mass 35% or less of a mass of the powder are kneaded to generate a plastic solid material containing a liquid. The solid material is extruded from a mold to plastically deform the solid material and a predetermined cross-sectional shape is imparted to the solid material. The solid material having the predetermined cross-sectional shape is sliced with a cutting edge so as to have a film shape having a predetermined thickness.

10 Claims, 16 Drawing Sheets

(58) Field of Classification Search
CPC ........ A61K 9/70; B26D 2210/02; B26D 7/01; B26D 7/0006
See application file for complete search history.

(56) References Cited

U.S. PATENT DOCUMENTS

| | | | | |
|---|---|---|---|---|
| 5,626,067 | A * | 5/1997 | Lothe | B26D 7/01 |
| | | | | 83/761 |
| 2004/0096569 | A1* | 5/2004 | Barkalow | A23L 27/79 |
| | | | | 426/660 |
| 2005/0136096 | A1 | 6/2005 | Davidson | |
| 2011/0236465 | A1 | 9/2011 | Hall et al. | |
| 2011/0277925 | A1* | 11/2011 | Xue | B29C 63/0034 |
| | | | | 156/245 |
| 2012/0093982 | A1* | 4/2012 | Tsukioka | A61K 9/006 |
| | | | | 426/531 |

FOREIGN PATENT DOCUMENTS

| | | | |
|---|---|---|---|
| JP | S56058448 | A | 5/1981 |
| JP | H03155755 | A | 7/1991 |
| JP | H04364120 | A | 12/1992 |
| JP | H07100903 | A | 4/1995 |
| JP | 2007077142 | A | 3/2007 |
| JP | 2008072915 | A | 4/2008 |
| JP | 2009061108 | A | 3/2009 |
| JP | 2013505251 | A | 2/2013 |
| JP | 2013249283 | A | 12/2013 |
| JP | 6050031 | B2 | 12/2016 |
| JP | 2017520625 | A | 7/2017 |
| JP | 2017530990 | A | 10/2017 |

* cited by examiner

METHOD OF PRODUCING EDIBLE FILM, FILM FORMULATION, AND EDIBLE FILM

TECHNICAL FIELD

The present invention relates to a method of producing an edible film, a film formulation, and an edible film.

BACKGROUND ART

Conventionally, for example, an edible film has been used for a film formulation described in Patent Document 1, a film-shaped confectionery, a film-shaped oral care product, and a film-shaped refrigerant. Since the edible film is put into an oral cavity, the edible film is made of a material that can be eaten. The biggest feature of the edible film is to have the film shape.

CITATION LIST

Patent Literature

Patent Document 1: JP6050031B

SUMMARY OF INVENTION

Technical Problem

As described in Patent Document 1, to mold the material that can be eaten in the thin film shape, a casting method is frequently used as the method of producing edible film. In the casting method, an edible material is dispersed or dissolved in a large amount of liquid, the liquid is developed, and after the edible material is thinly extended, the edible material is dried to produce the edible film.

However, to produce the edible film by casting method, a large loss of material that is not produced as a final product occurs.

An object of the present invention is to provide a method of producing an edible film that reduces a loss of material generated at production of an edible film. Furthermore, the object is to provide a film formulation or an edible film having a predetermined function imparted by use of the production method.

Solution to Problem

Some aspects will be described below as means to solve the problems. These aspects can be combined arbitrarily as necessary.

A method of producing an edible film according to one aspect of the present invention is a method of producing an edible film having a predetermined film shape. The method includes kneading an edible powder formed of particles smaller than a film thickness, a predetermined component, and an edible liquid having a mass 35% or less of a mass of the powder to generate a plastic solid material containing a liquid; extruding the solid material from a mold to plastically deform the solid material and imparting a predetermined cross-sectional shape to the solid material; and slicing the solid material having the predetermined cross-sectional shape with a cutting edge so as to have the film shape having a predetermined thickness.

In the method of producing the edible film configured in this manner, the liquid contained in the material in the production process is less than that of a casting method. Therefore, the material is less likely to adhere to, for example, production equipment. Thus, a loss of the material in the entire production process of the edible film can be reduced.

The method of producing the edible film can adjust a temperature of the solid material sliced with the cutting edge. When configured in this manner, hardness of the solid material at the slice can be regulated, and accuracy of slicing the solid material with the cutting edge can be improved.

The method of producing the edible film allows causing the solid material after the slice to pass through a clearance between the cutting edge and a restricting member having a surface along the cutting edge at the slice with the cutting edge.

When configured in this manner, curling of the film-shaped solid material after the slice can be suppressed.

The method of producing edible film can be configured as follows. The predetermined cross-sectional shape is an annular shape. The film shape is an annular shape. When configured in this manner, compared with a production method that punches part of the solid material to form the annular shape, the edible film having the annular film shape can be provided with less material loss.

The method of producing the edible film can be configured as follows. In the method of producing the edible film, the solid material contains a first solid material and a second solid material in which at least one of the powders, the predetermined components, and the liquids are different from one another. The method includes simultaneously extruding the first solid material and the second solid material from the mold such that a first region where the first solid material is present and a second region where the second solid material is present are formed in the predetermined cross-sectional shape, and slicing the solid material with the cutting edge such that the region where the first solid material is present and the region where the second solid material is present are divided in the film shape. When configured in this manner, a single edible film can have a function of the first solid material and a function of the second solid material in combination and can have a function that cannot be imparted when the entire edible film is produced with the same solid material.

A film formulation according to one aspect of the present invention includes a base and a medicinal component. The base has a film shape and is made of an edible solid. The medicinal component is kneaded into the base. The base has an annular planar shape.

The film formulation configured in this manner allows reducing a risk of suffocation even when the film formulation is swallowed and enters a throat by mistake when the film formulation is applied inside an oral cavity, as a hole bored at a center of the ring serves as an air pathway.

An edible film according to one aspect of the present invention includes a composition and a component. The composition constitutes a film-shaped base made of an edible solid. The component is kneaded into the base. When the composition contains a first composition and a second composition different from one another, the first composition and the second composition are separately kneaded into two regions different from one another in the base. When the component contains a first component and a second component different from one another, the first component and the second component are separately kneaded into two regions different from one another in the base.

The edible film configured in this manner can combine functions provided to the two regions and achieve the function that cannot be achieved when the entire edible film is made of the same solid material.

Advantageous Effects of Invention

The method of producing edible film of the present invention allows reducing a loss of material generated at production of the edible film. The film formulation or the edible film of the present invention can exhibit the function not provided to a film formulation or an edible film in which an inside of an outer periphery is uniform.

Figure 1:
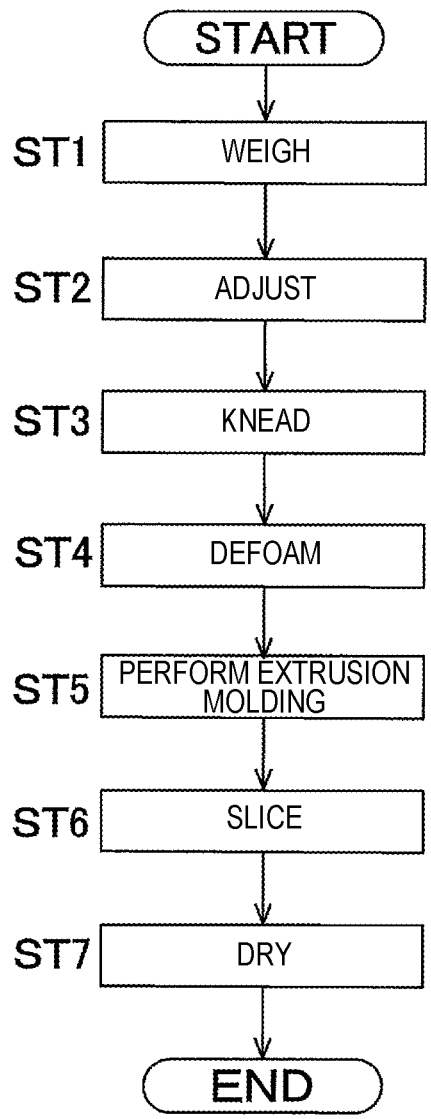
FIG. 1 is a flowchart depicting an example of a method of producing edible film according to an embodiment.

DESCRIPTION OF EMBODIMENTS (1) Method of Producing Edible Film

An overview of the method of producing an edible film according to an embodiment of the present invention will be described using FIG. 1.

First, a material used for producing an edible film is weighed (Step ST1). The material of the edible film is mainly an edible powder as a main material of a base of the edible film, an edible liquid to solidify the powder and form a solid material, and a predetermined component required for a purpose of the edible film. However, an auxiliary material may be added to the solid material other than these main materials. In Step ST1, the powder, the liquid, and the predetermined component that should be contained in a predetermined amount of the solid material are weighed. Each of the powder, the liquid, and the predetermined component may be one kind, or may be a plurality of kinds in some cases. When a plurality of components, such as a first component and a second component, are contained in the edible film, for example, they are weighed for each component.

The edible powder is a material for forming the base of the edible film. As the edible powder, for example, an edible organic compound or an edible inorganic compound can be used. The edible organic compound includes, for example, edible carbohydrate, edible protein, and edible fat. The edible carbohydrate includes, for example, edible disaccharide, edible polysaccharide, edible sugar alcohol, and edible dietary fiber. The edible polysaccharide includes, for example, alginic acid, sodium alginate, pregelatinized starch, carrageenan, agar, xanthan gum, potato starch, cellulose, and pullulan. The edible dietary fiber includes pectin and cellulose. The edible disaccharide includes, for example, refined white sugar. The edible sugar alcohol includes, for example, sorbitol. The edible protein includes gelatin. The edible organic compound other than carbohydrate, protein, or fat includes, for example, polyvinyl alcohol (PVA), polyvinyl pyrrolidone (PVP (povidone)), polyethylene oxide, and macrogol (polyethylene glycol). Additionally, these edible derivatives include, for example, a derivative of saccharide, a cellulose derivative, a derivative of polyvinyl alcohol, and a derivative of sorbitol. The derivative of saccharide includes, for example, a sucrose fatty acid ester. The cellulosic derivative includes ethyl cellulose, carmellose (CMC), carmellose sodium, and hypromellose (HPMC). The derivative of sorbitol includes sorbitan and a sorbitan fatty acid ester (polysorbate). The edible inorganic compound includes titanium oxide and talc. A particle size of the powder used as the material of the edible film is smaller than a thickness of the edible film.

The edible liquid includes, for example, water, edible alcohol, edible glycol, glycerin, and edible oil. The edible alcohol includes, for example, ethyl alcohol. The edible glycol includes propylene glycol.

The predetermined component includes, for example, a medicinal component to provide a function as a medical agent to the edible film, a taste component to impart a taste to the edible film, a pigment component to color the edible film, a nutritional component to impart a nutrient to the edible film, and an aroma component that imparts an aroma to the edible film.

The auxiliary material includes, for example, a binder that binds particles to one another, an excipient that increases a size of the edible film for ease of handling, a disintegrant that imparts disintegrability to the edible film, a flavoring agent to adjust the taste, a wetting agent that prevents drying and improves flexibility of the film, a colorant to provide coloring, and an emulsifier for excellent mixture of the components.

The binder includes, for example, amylopectin, sodium alginate, pregelatinized starch, carmellose, carmellose sodium, agar, glycerin, crystalline cellulose, high molecular polyvinylpyrrolidone, wheat starch, rice starch, a sucrose fatty acid ester, purified gelatin, purified shellac, refined white sugar, gelatin, soy lecithin, low substituted hydroxypropylcellulose, dextrin, concentrated glycerin, crystalline cellulose, hydroxyethyl cellulose, hypromellose, pullulan, pectin, povidone, polyethylene oxide, polysorbate, polyvinyl alcohol, macrogol, D-mannitol, and methyl cellulose.

The excipient includes, for example, alginic acid, sodium alginate, pregelatinized starch, ethyl cellulose, carrageenan, carmellose, carmellose sodium, agar, glycerin, croscarmellose sodium, crospovidone, magnesium silicate, crystalline cellulose, flour, wheat starch, rice flour, rice starch, titanium oxide, a sucrose fatty acid ester, refined white sugar, gelatin, powdered skim milk, talc, dextran, dextrin, potato starch, hypromellose, pullulan, pectin, povidone, polyethylene oxide, polysorbate, polyvinyl alcohol, macrogol, maltitol, maltose, and methyl cellulose.

The disintegrant includes, for example, alginic acid, pregelatinized starch, carmellose, carmellose sodium, agar, croscarmellose sodium, crospovidone, crystalline cellulose, wheat starch, rice starch, a sucrose fatty acid ester, gelatin, dextrin, cornstarch, potato starch, hydroxypropyl cellulose, hypromellose, povidone, polyethylene oxide, polysorbate, macrogol, magnesium aluminometasilicate, methyl cellulose, and sodium lauryl sulfate.

The flavoring agent includes, for example, aspartame, DL-alanine, erythritol, a reduced maltose starch syrup, xylitol, citric acid hydrate, sodium citrate hydrate, glycerin, succinic acid, sodium succinate, acetic acid, saccharin, tartaric acid, sodium tartrate, sucralose, thaumatin, sodium hydrogen carbonate, capsicum, trehalose, white sugar, honey, povidone, D-mannitol, and menthol.

The wetting agent includes, for example, a reduced starch syrup, glycerin, a sucrose fatty acid ester, D-sorbitol, propylene glycol, polysorbate, macrogol, and methyl cellulose.

The colorant includes, for example, titanium oxide, edible dye, and talc.

The emulsifier includes, for example, polysorbate, refined soy lecithin, medium chain fatty acid triglyceride, and sodium lauryl sulfate.

For example, a mass of the liquid is 35% or less of a mass of the powder. When the mass of the liquid is excessively large, the extruded solid material becomes excessively soft or sticks to a cutting edge for slice, and therefore the slice with the cutting edge is difficult.

Next, the material of the solid material to be sliced is adjusted (Step ST2). The material is designed in a state appropriate for putting into a kneader 10 in kneading after the adjustment. A plurality of types of liquids are contained in the material in some cases, a plurality of types of liquids are contained in some cases, and a plurality of types of components are contained in the predetermined component in some cases. In the adjustment of the material, for example, the predetermined component is added to the liquid. In the adjustment of the material, the powder, the liquid, and the predetermined component are properly mixed.

Figure 2:
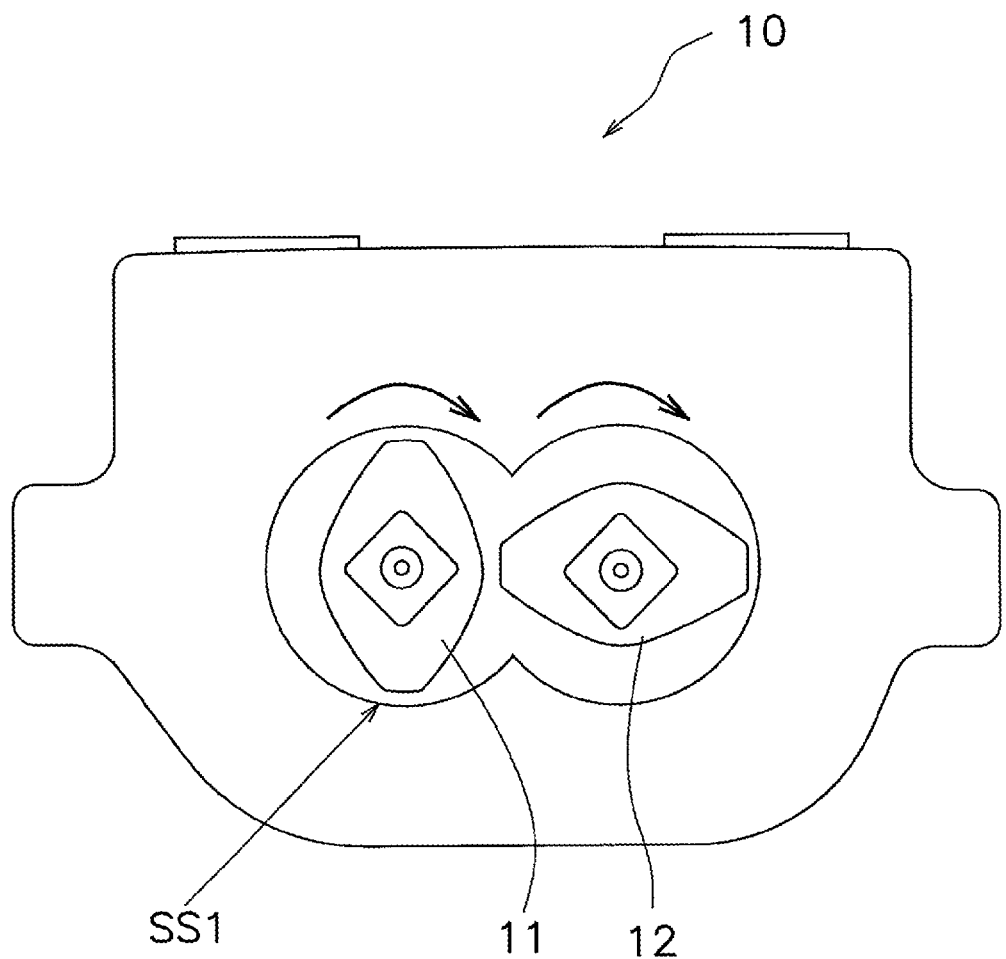
FIG. 2 is a cross-sectional view illustrating an example of a kneader.

The adjusted material is put into the kneader 10 as illustrated in FIG. 2, for example, and kneaded (Step ST3). The put material is kneaded in a space SS1 where two propellers 11 and 12 rotate in the directions of the arrows by the kneader 10. The kneader 10 performs kneading so that the edible powder, the edible liquid, and the predetermined component become uniform. Kneading these materials allows obtaining a plastic solid material, such as a clay, to which water content is added. However, the type of the kneader 10 is not limited to the one illustrated in FIG. 2. The kneader 10 illustrated in FIG. 2 is a batch type, but may be a continuous type.

Figure 3:
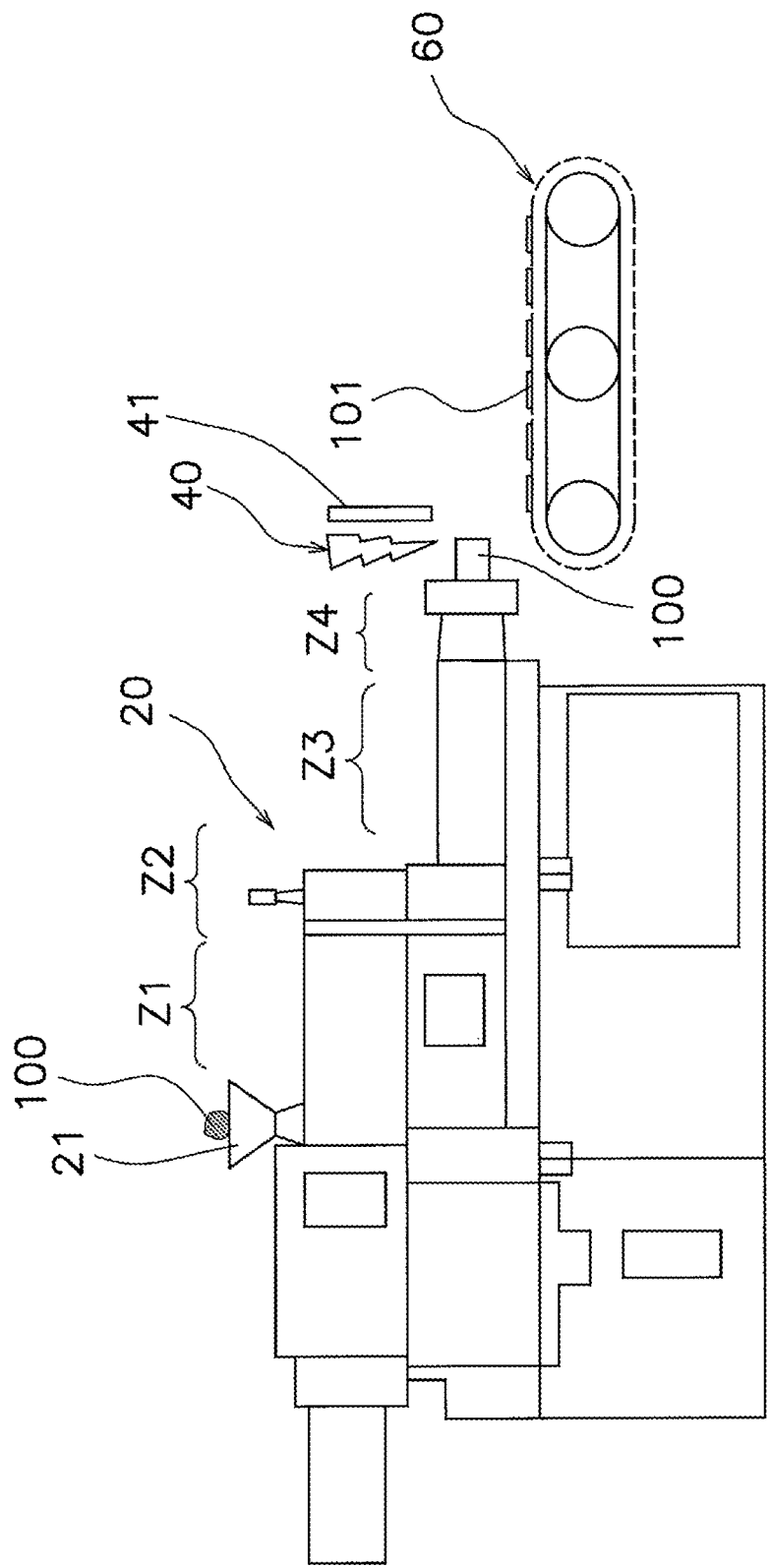
FIG. 3 is a schematic diagram for explaining a relationship between a vacuum clay kneader, a mold, and a cutting edge.
Figure 4:
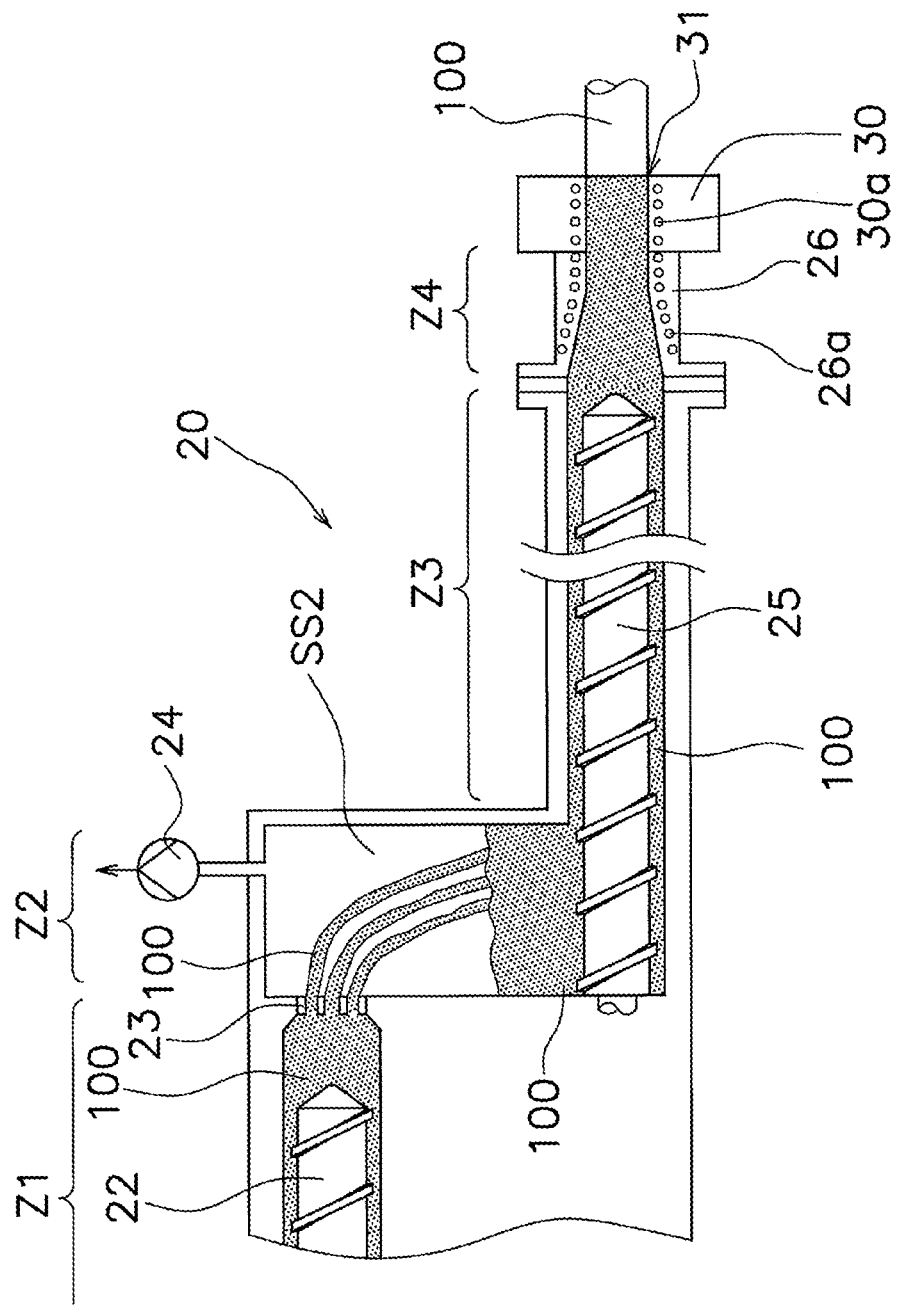
FIG. 4 is a partially enlarged cross-sectional view illustrating a portion of the clay kneader and the mold.

Air is mixed in the solid material obtained by kneading in the process of kneading. Therefore, to remove the air in the solid material, deaeration (or referred to as defoaming) is performed (Step ST4). By deaerating a solid portion and reducing bubbles in the solid material, the solid portion can be dense, thereby ensuring the solid material that is less likely to be damaged can be obtained. For deaeration, a vacuum clay kneader 20 as illustrated in FIG. 3 and FIG. 4 is preferably used. The vacuum clay kneader 20 allows extrusion molding in addition to deaeration. Note that a mold 30 is mounted to a distal end portion of the clay kneader 20. The clay kneader 20 to which the mold 30 or a die is thus mounted for molding is referred to as an extruder in some cases.

Extrusion molding of a solid material 100 is performed with the clay kneader 20 and the mold 30 (Step ST5). The vacuum clay kneader 20 is provided with mainly four first zone Z1, second zone Z2, third zone Z3, and fourth zone Z4 between an input port 21 and the mold 30. The first zone Z1 starting immediately after the input port 21 is an area where the solid material 100 is carried to the second zone Z2 while kneaded. When air is removed from the solid material 100 in the second zone Z2, the solid material 100 is preferably thin as much as possible. Thus, the first zone Z1 is also an area where pressure can be generated such that the solid material 100 can be divided into a plurality of the solid materials 100 and extruded at a boundary with the second zone Z2. For example, a screw 22 for extrusion is disposed in the first zone Z1. The screw 22 may be one, but may be two or more. FIG. 4 illustrates the solid materials 100 being divided into the plurality of solid materials 100 and extruded from the first zone Z1 to the second zone Z2. The first zone Z1 and the second zone Z2 are partitioned by a partition plate 23 having a plurality of holes.

A space SS2 having an air pressure lower than atmospheric pressure is provided in the second zone Z2. A vacuum pump 24 is connected to the space SS2. The air is removed from the space SS2 with the vacuum pump 24 to lower the air pressure in the space SS2.

A screw 25 for extrusion extends from the second zone Z2 to the third zone Z3. The solid material 100 deaerated in the second zone Z2 is pushed into the mold 30 through a cooling jacket 26 with the screw 25. A passage of the cooling jacket 26 through which the solid material 100 passes has a passage cross-sectional surface that decreases in size as approaching the mold 30 such that pressure is applied to the solid material 100. The cooling jacket 26 and the mold 30 include flow paths 26a and 30a of cooling water for cooling the solid material 100 that increases a temperature due to, for example, friction heat in the third zone Z3. The fourth zone Z4 is an area for passing through the cooling jacket 26. In other words, a cooling unit that cools the solid material 100 that has increased by the screw 25 for extrusion is provided between the mold 30 and the screw 25. Here, the case where the cooling unit is configured by the cooling jacket 26 has been described, but the cooling unit may be configured by an instrument other than the cooling jacket 26. The cooling jacket 26 and the mold 30 decrease the solid material 100 in temperature to, for example, 50° C. or more by the screw 25 down to 25° C. to 35° C. The temperature after the cooling is appropriately set according to the kinds and the compound ratios of the materials constituting the solid material 100.

By lowering the temperature of the solid material 100, the solid material 100 can have hardness at which the solid material 100 can hold its shape after being extruded from the mold 30. However, the solid material 100 in the mold 30 has hardness at which the solid material 100 can cause plastic deformation when extruded.

Figure 5:
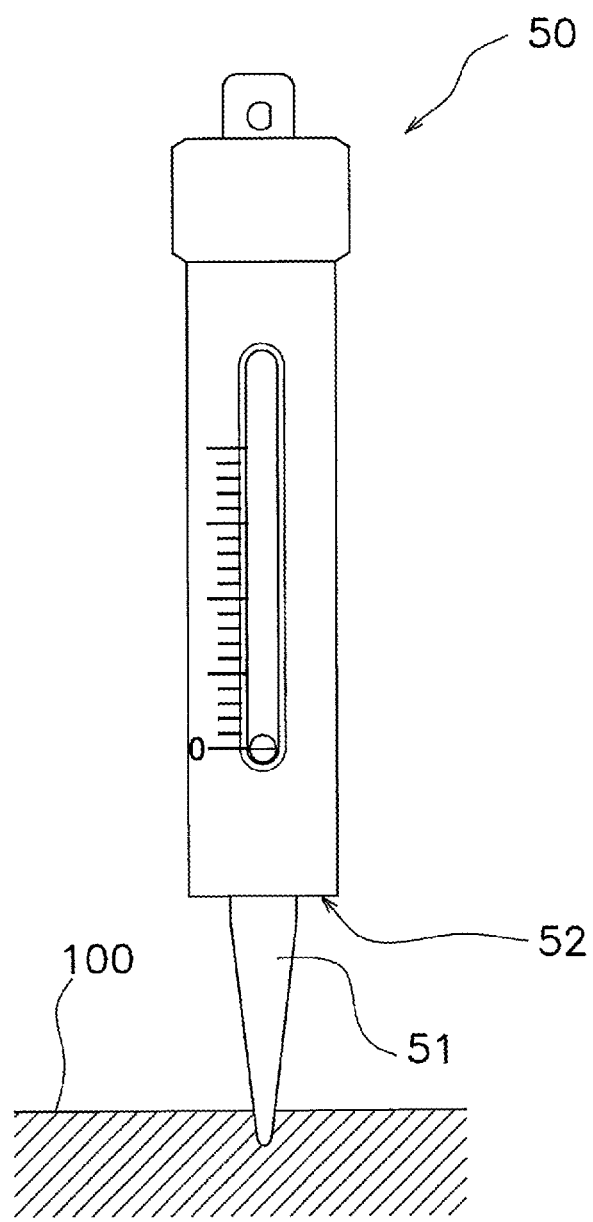
FIG. 5 is a front view of a clay hardness meter.

In addition, by lowering the temperature of the solid material 100, the solid material 100 has a hardness at which the solid material 100 can be excellently cut with a cutting edge 40. The solid material 100, which is cut with the cutting edge 40, preferably has a hardness of 10 or more and 16 or less with a CRAY HARDNESS TESTER 50 (available from NGK INSULATORS, LTD) illustrated in FIG. 5. When the solid material 100 is excessively hard, fine chips are generated and attach to the edible film as foreign objects. Further, the excessively hard solid material 100 wears the cutting edge 40 prematurely. A lower end surface 52 of the body of the clay hardness meter 50 is brought into contact with the solid material 100, and the hardness is measured by a depth that a conical tip terminal 51 sinks by being pushed with a spring biased by the contact. The harder the measurement target is, the more that the tip terminal 51 does not sink and the larger the value of the clay hardness meter 50 is.

Next, the solid material 100 extruded from the mold 30 is sliced with the cutting edge 40 (Step ST6). The slice direction is, for example, a direction intersecting with the central axis of the columnar solid material 100. In the embodiment, the solid material 100 is sliced in the direction orthogonal to the central axis. However, the slice direction is not limited to the orthogonal direction, and the solid material 100 may be, for example, sliced obliquely to form an elliptical planar shape. The thin portion of the cutting edge 40 is physically pressed against the solid material 100 to cut the solid material 100. The cutting edge 40 also includes, for example, a wire stretched like a bowstring of a bow. The cutting edge 40 may be moved in a direction other than the slice direction, and may, for example, ultrasonically oscillate.

Figure 6:
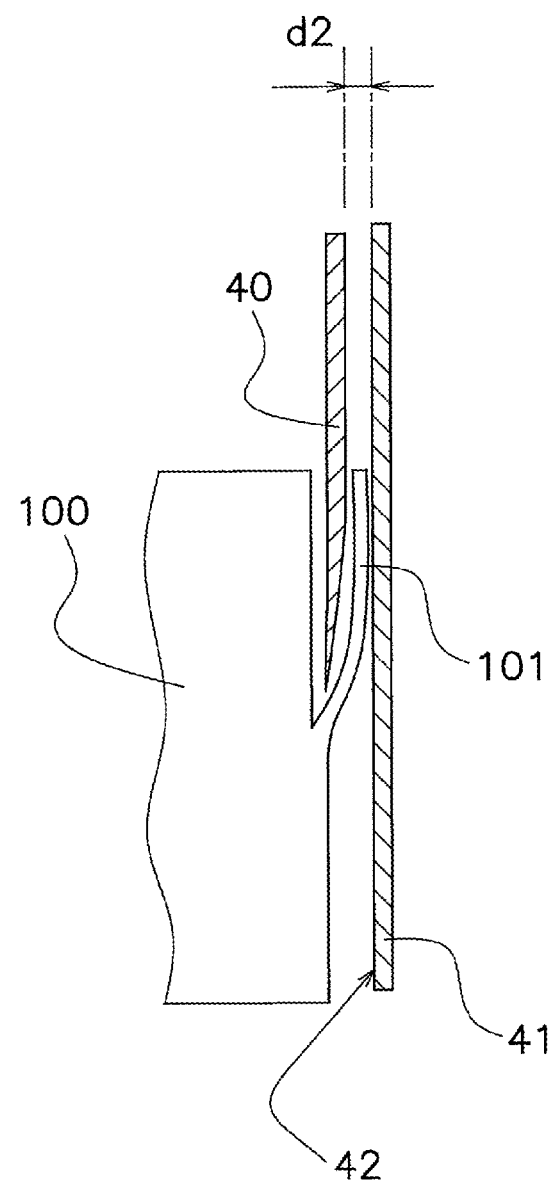
FIG. 6 is a partially enlarged cross-sectional view for describing a relationship between the cutting edge and a pressing plate.

As illustrated in FIG. 6, a surface 42 of a pressing plate 41 as a restricting member is disposed along the cutting edge 40. A fluorine resin is preferably used for the pressing plate 41. However, the material of the restricting member is not limited to the resin. The surface 42 of the pressing plate 41 preferably has fine irregularities for ease of sliding of a sliced solid material 101 having the film shape. To suppress a curl of the film-shaped solid material 101, a size d2 of a clearance between the cutting edge 40 and the surface 42 of the pressing plate 41 is preferably thicker than and twice or less of a thickness d1 (see FIG. 7C) of the film shape. Suppressing the curl of the edible film allows an effect of enhancing an expected commercial value of the edible film. Note that the solid material 101 for edible film that does not cause a problem even curled or the solid material 101 made of a material that is less likely to curl may be sliced with the cutting edge 40 with the pressing plate 41 removed.

Figure 7A:
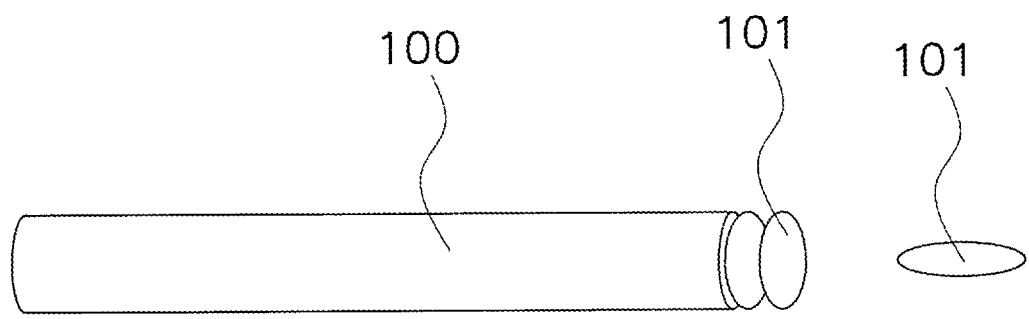
FIG. 7A is a schematic diagram illustrating an example of a solid material extruded from the mold and sliced.
Figure 7B:
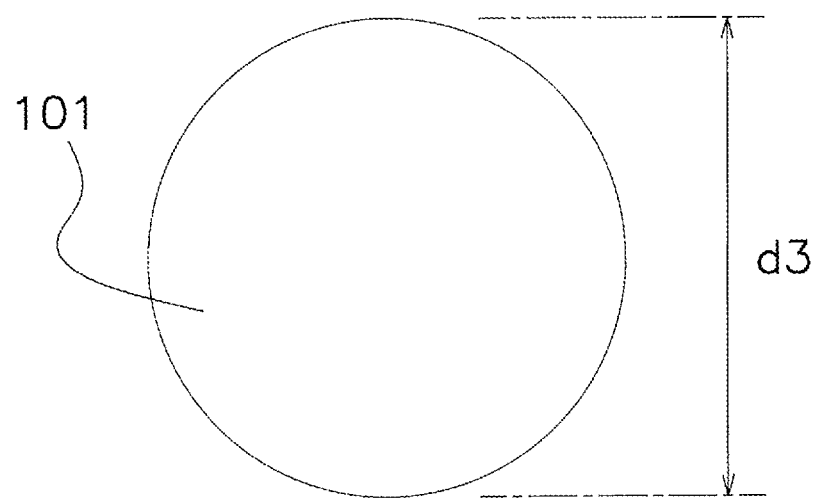
FIG. 7B is a plan view illustrating an example of the sliced solid material.
Figure 7C:
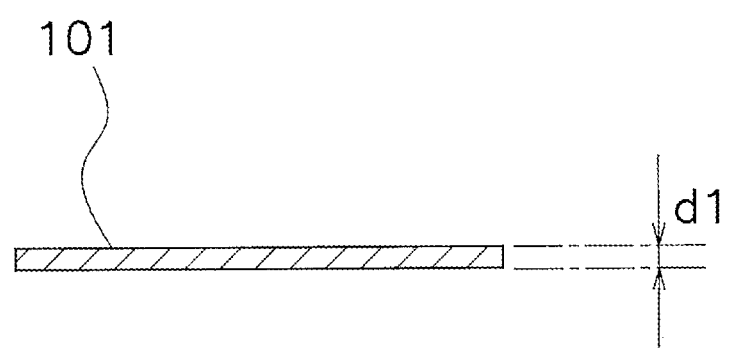
FIG. 7C is a cross-sectional view illustrating an example of the sliced solid material.

A circular hole 31 into which the solid material 100 is extruded is provided in the mold 30. Thus, the solid material 100 extruded from the mold 30 has a columnar shape as illustrated in FIG. 7A. The film-shaped solid material 101 has a diameter d3 (see FIG. 7B) of, for example, 30 mm, and the thickness d1 (see FIG. 7C) of, for example, 0.1 mm. Here, the case where the thickness d1 is 0.1 mm is described, but the thickness d1 is preferably 0.5 mm or less, and further preferably 0.3 mm or less. The edible film having a thickness of 0.5 mm or less is excellent in portability and uncomfortable feeling when the edible film is put into an oral cavity is small. The edible film having the thickness d1 of 0.5 mm or less or further 0.3 mm or less improves solubility or disintegrability, and therefore is suitable for application of quick dissolution or application of rapid disintegration.

The solid material 100 may be sliced while extruded from the mold 30, and may be sliced after separating the solid material 100 extruded from the mold 30 from the mold 30. For slicing after the separation from the mold 30, the temperature of the solid material 100 may be adjusted to adjust the hardness of the solid material 100 after separating the solid material 100 from the mold 30. For example, the solid material 100 may be placed in a room at a predetermined temperature for a predetermined period of time and may be sliced with the cutting edge 40 when the temperature of the solid material 100 reaches a predetermined temperature.

The sliced film-shaped solid material 101 is carried to, for example, a dryer (not illustrated) by a belt conveyor 60 to be dried (Step ST7). The edible film is completed by drying. The edible film is packed and shipped after drying. Note that the drying step may be omitted depending on the type of the edible film.

(2) Edible Film

Figure 8:
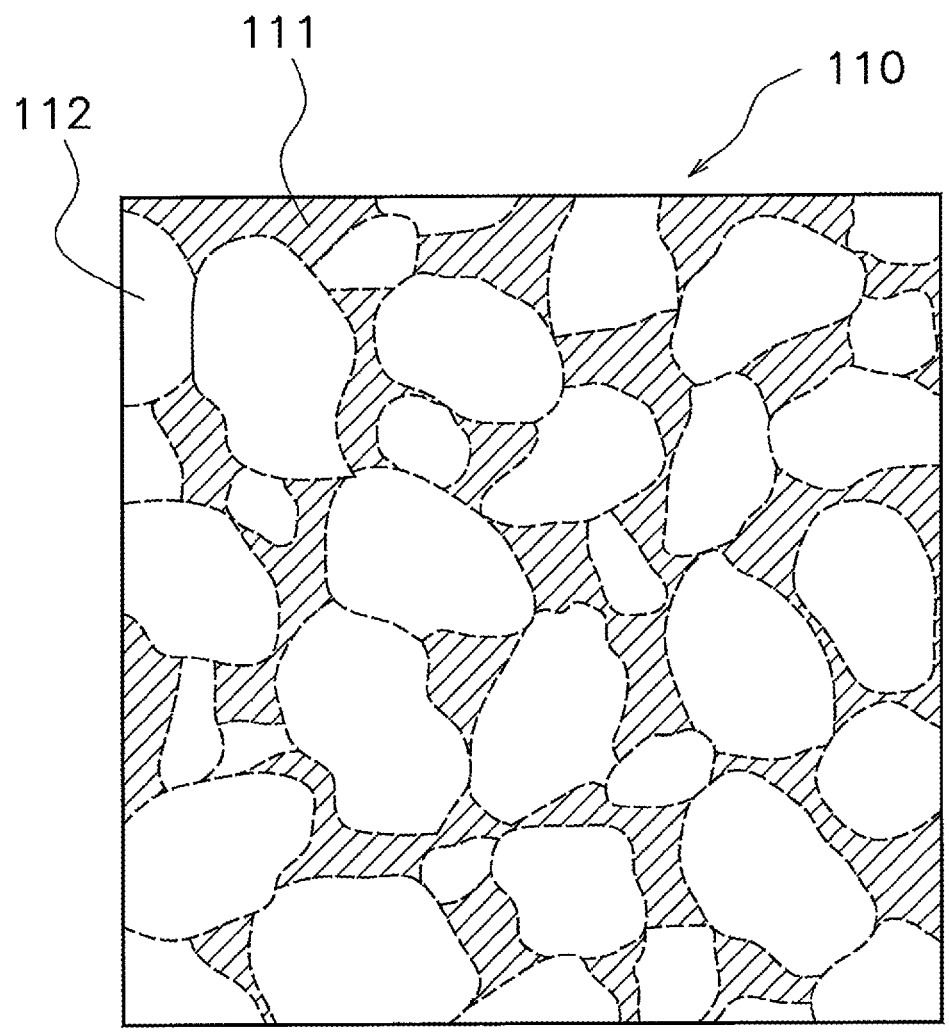
FIG. 8 is a schematic view for describing a structure of an edible film.

FIG. 8 schematically illustrates a portion of an enlarged edible film 110. In the method of producing an edible film of the present embodiment, for example, when the medicinal component is not readily soluble in the liquid, the medicinal component is not dissolved at kneading in a clay shape and can be kneaded in the form of particles. Therefore, the edible film 110 can be shaded in some cases. In a region where a particle size level of the powder is substantially fine, portions 111 where a concentration of the medicinal component is comparatively high, which are indicated by the diagonal lines in FIG. 8, and portions 112 where a concentration of the medicinal component is low where the diagonal lines are not drawn can be formed. The amount of liquid used is less than that of the casting method. Accordingly, while the conventional process casts a large amount of liquid and forms a film shape without difference in concentration, in the process by kneading, the amount of liquid is less than the amount of powder and therefore the powder is directly kneaded in the form of particles. Thus, a film formulation having a greater difference in concentration than that of the casting method is obtained in some cases. By thus disposing concentrations of the predetermined components in a sea-island structure, a new function that is not provided conventionally can be added to the edible film 110 in some cases.

In contrast, in a case where the medicinal component is easily soluble in the liquid, when the medicinal component is kneaded in a clay shape, the medicinal component can be kneaded in the dissolved state. Accordingly, the medicinal component can be easily uniformly kneaded without generating the shade with the concentrations as described above.

(3) Modified Example (3-1) Modified Example A

In the embodiment, the case in which the film-shaped solid material 101 has the circular shape (see FIG. 7B) has been described. Drying the solid material 101 having a circular planar shape allows obtaining an edible film having a circular planar shape.

Figure 9A:
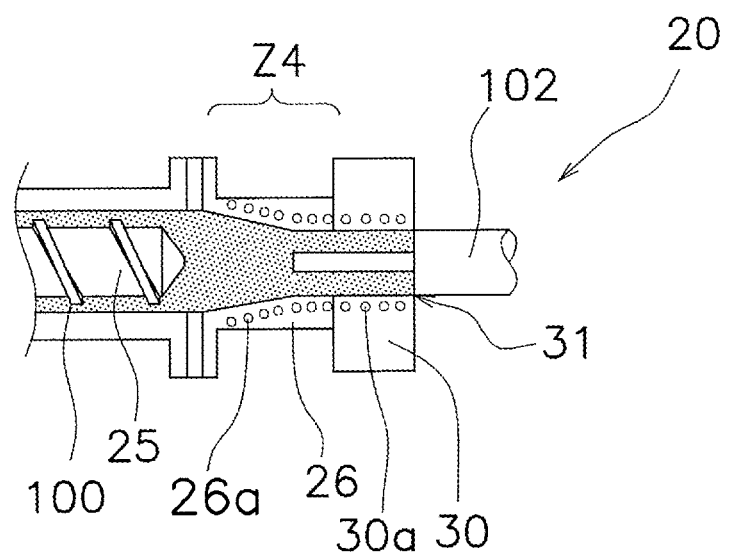
FIG. 9A is a partially enlarged cross-sectional view of a periphery of the mold for describing a production method of Modified Example A.
Figure 9B:
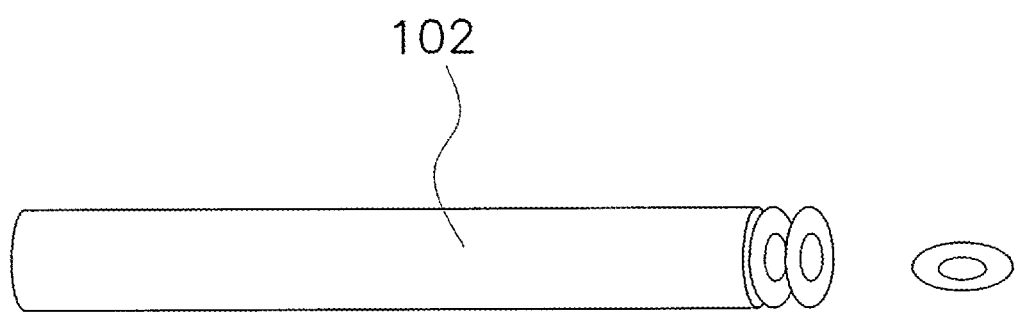
FIG. 9B is a schematic view illustrating an example of a solid material extruded from the mold and sliced.

However, the shape of the edible film that can be produced by extrusion molding is not limited to a shape in which an inside of an outer periphery is hollow, such as a circular shape, a rectangular shape, and a polygonal shape. As illustrated in FIG. 9A, the hole 31 of the mold 30 can be formed in a doughnut shape, and a cylindrical solid material 102 can be extruded. When the cylindrical solid material 102 is sliced with the cutting edge 40, as illustrated in FIG. 9B, an annular-shaped film formulation 120 having a hole 121 at a center of a base 125 can be obtained. The film formulation 120 includes a medicinal component as the predetermined component.

There may be not only one hole 121, but also a plurality.

(3-2) Modified Example B

In the embodiment, the case in which the predetermined component is uniformly dispersed in the one entire film-shaped edible film 110 has been described. However, for example, when the predetermined component contains the first component and the second component different from one another, as illustrated in FIG. 10C, the first component may be kneaded into only a first region 131 of a base 135 of an edible film 130, and the second component may be kneaded into only a second region 132 of the base. Note that a third component different from the first component and the second component may be contained in both the first region 131 and the second region 132. In addition, for example, when the powder contains a first powder and a second powder different from one another, as illustrated in FIG. 10C, a first composition of the first powder may be kneaded into only the first region 131 of the base 135 of the edible film 130, and a second composition of the second powder may be kneaded into only the second region 132 of the base. In this case, the first composition is a composition that constitutes the first region 131 of the base 135, and the second composition is a composition that constitutes the second region 132 of the base 135. Note that other regions, such as a third region and a fourth region, different from the first region 131 and the second region 132 may be formed in the base 135. Also, a third composition different from the first composition and the second composition may be contained in both the first region 131 and the second region 132.

For example, a case in which the edible film 130 is a seasoning agent, a pungent component is kneaded as the first component into the first region 131 and the first region 131 is colored in red, a taste component is kneaded as the second component into the second region 132 and the second region 132 is colored in yellow will be described. When the edible film 130 is put into a pot for seasoning and the pungent component is desired to be suppressed, a portion of the first region 131 colored in red is cut with cooking scissors to reduce an area of the first region 131. When the edible film 130 is put into a pot for seasoning, compared with the case of not reducing the area of the first region 131, the pungent component can be reduced.

Figure 10A:
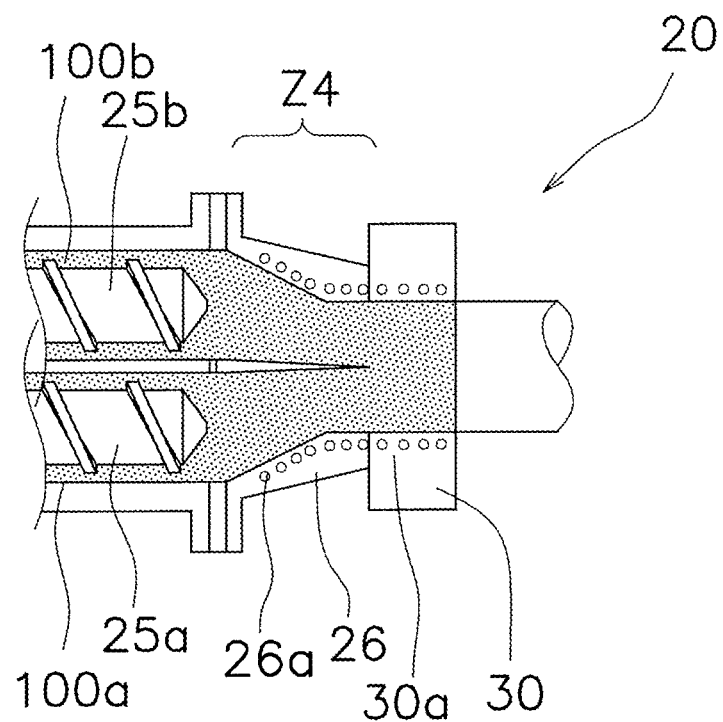
FIG. 10A is a partially enlarged cross-sectional view of a periphery of the mold for describing a production method of Modified Example B.

As described above, to separate the components kneaded into the first region 131 and the second region 132, as illustrated in FIG. 10A, a first solid material 100a and a second solid material 100b as solid materials in which at least one of powders, predetermined components, and liquids are different from one another are prepared. Then, using different screws 25a and 25b, the first solid material 100a and the second solid material 100b are simultaneously extruded from the mold 30 such that a first region 103a where the first solid material 100a is present and a second region 103b where the second solid material 100b is present are formed in the predetermined cross-sectional shape of an extruded solid material 103. The solid material 103 is sliced with the cutting edge 40 such that a region 141 where the first solid material 100a is present and a region 142 where the second solid material 100b is present are divided in the film shape.

(3-3) Modified Example C

In the method of producing the edible film of the embodiment, as illustrated in FIG. 1, defoaming is performed before the extrusion molding (Step ST4). However, the defoaming process may be omitted in the method of producing the edible film. When air bubbles are contained in the solid material and molded in a film shape, the solubility and disintegrability of the edible film can be improved.

(4) Features 4-1

In the method of producing the edible film 110 or 130 or the film formulation 120, which is one kind of an edible film, having the above-described predetermined film shape (the circular film shape in the above-described case), a proportion of the liquid contained in the material in the production process before the processing to form the film shape is less than that of the conventional casting method. Therefore, a proportion of the material that adheres to, for example, production equipment (the kneader 10 and the clay kneader 20) and is not contained in the edible film 110 or 130 or the film formulation 120 can be reduced. Thus, a loss of the material in the production process of the edible films 110 and 130 and the film formulation 120 can be reduced.

For example, compared with the conventional casting method, when a certain specific edible film is produced, a material loss occurs by about 10% in weighing, liquid adjustment, mixture, and defoaming in the casting method. A material loss of about 20% occurs in coating of flowing a material over a drum or a plastic film. A material loss of about 10% occurs in the subsequent drying, slitting, cutting, and packing. In contrast, when the specific edible film described above is produced, in the method of producing the edible film of the embodiment, a material loss of about several percent occurs in weighing, adjustment, and kneading. In defoaming and extrusion molding, a material loss of about 10% or less occurs. A material loss of about several percent occurs in the subsequent slice, drying, and packing. Compared with the method of producing the edible film of the embodiment in the same production of the edible film, a loss of the material can be reduced to the about the half compared with the casting method.

4-2

The above-described method of producing the edible film 110 or 130 or the film formulation 120 adjusts the temperature of the plastic solid material 100 or the first solid material 100a and the second solid material 100b sliced with the cutting edge 40 by cooling with the cooling jacket 26. Thus, the hardness of the plastic solid material 100, the first solid material 100a, and the second solid material 100b are adjusted to 10 to 16 with the NGK clay hardness meter 50. As a result, accuracy of the slice can be improved when the plastic solid material 100, the first solid material 100a, and the second solid material 100b are sliced with the cutting edge 40.

4-3

The above-described method of producing the edible film 110 or 130 or the film formulation 120 causes the solid material 100 or the first solid material 100a and the second solid material 100b after slice to pass through the clearance between the cutting edge 40 and the pressing plate 41, which is the regulating member having the surface 42 along the cutting edge 40, at slice with the cutting edge 40. Accordingly, deformation of the solid material 101 having the film shape is regulated with the cutting edge 40 and the pressing plate 41. As a result, the curl of the film-shaped solid material 101 after the slice is suppressed.

4-4

Figure 9C:
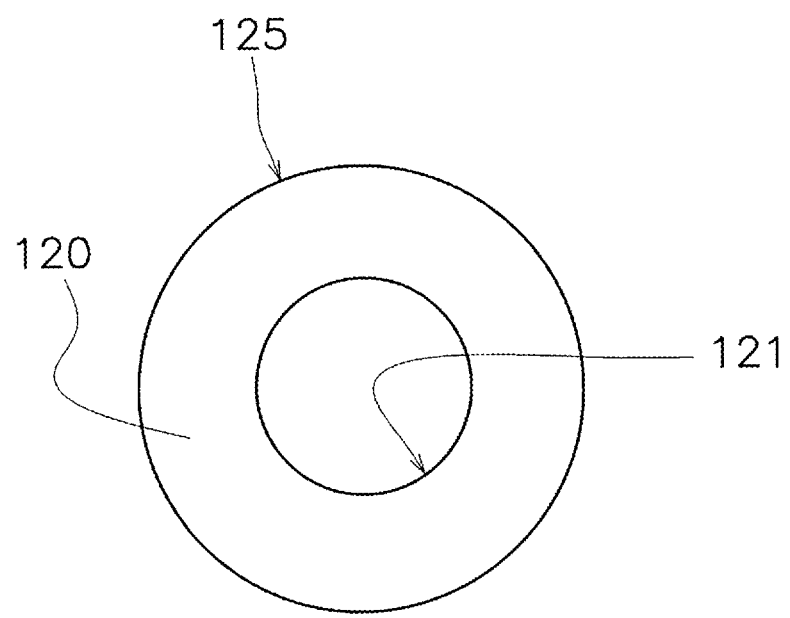
FIG. 9C is a plan view illustrating an example of a configuration of a film formulation.

According to the production method of the modified example A described using FIG. 9A, FIG. 9B, and FIG. 9C, the cross-sectional shape of the solid material 102 extruded from the mold 30 is a circular ring shape. However, the cross-sectional shape is not limited to the case of the circular ring shape, and, for example, the outer circumference may be a polygonal shape, such as a quadrangle shape. In the case illustrated in FIG. 9C, the film formulation 120 also has a circular ring shape. When configured in this manner, compared with a production method that punches part of the solid material to form the annular shape, the film formulation 120 as the edible film having the annular film shape can be provided with less material loss.

The film formulation 120 having the annular planar shape allows reducing a risk of suffocation even when the film formulation 120 is swallowed up to a throat by mistake when the film formulation 120 is applied to inside an oral cavity, as the hole 121 bored at a center of the ring serves as a path of air.

4-5

Figure 10B:
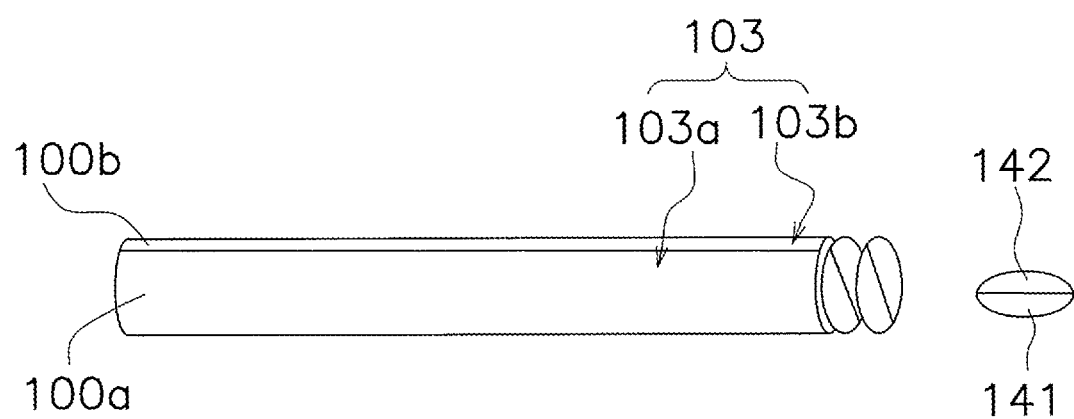
FIG. 10B is a schematic view illustrating an example of a solid material extruded from the mold and sliced.
Figure 10C:
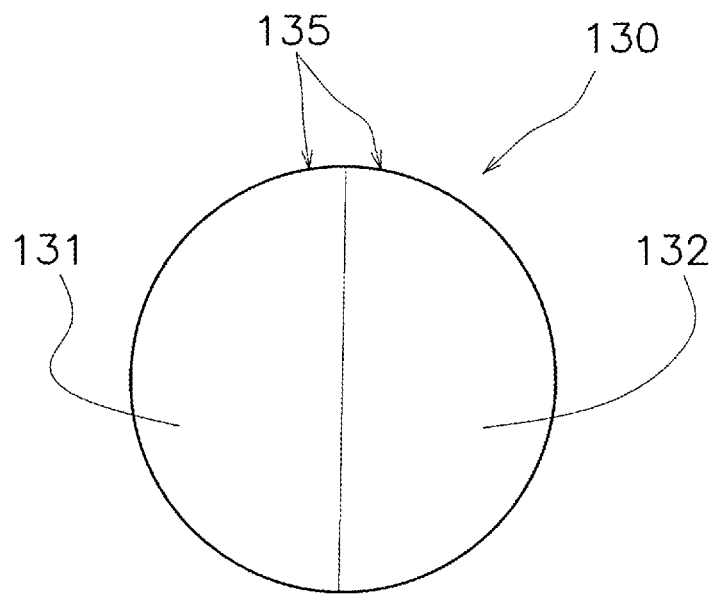
FIG. 10C is a plan view illustrating an example of a configuration of an edible film.

The production method of Modified Example B described with reference to FIG. 10A, FIG. 10B, and FIG. 10C uses the first solid material 100a and the second solid material 100b in which at least one of the powders, the predetermined components, and the liquids are different from one another to produce the edible film 130. The first solid material 100a and the second solid material 100b are simultaneously extruded from the mold 30 such that the first region 103a where the first solid material 100a is present and the second region 103b where the second solid material 100b is present are formed in the predetermined cross-sectional shape. Thereafter, the solid material 103 is sliced with the cutting edge 40 such that the region 141 where the first solid material 100a is present and the region 142 where the second solid material 100b is present are divided in the film shape.

The edible film 130 thus produced can be configured such that the first component is kneaded into only the first region 131 of the base 135 and the second component is kneaded into only the second region 132 of the base 135. Alternatively, the composition of the first powder can be kneaded into only the first region 131 of the base 135 and the composition of the second powder can be kneaded into only the second region 132 of the base 135. The edible film 130 can combine the function of the first region 131 and the function of the second region 132 and achieve the function that cannot be achieved when the one entire edible film is made of the same solid material.

Although one embodiment of the present invention is described above, the present invention is not limited to the above-described embodiments, and various modifications can be made without departing from the gist of the invention. In particular, the plurality of embodiments and modified examples described herein can be combined arbitrarily with one another as necessary.

REFERENCE CHARACTER LIST

10 Kneader
20 Clay kneader
30 Mold
40 Cutting edge
41 Pressing plate
100, 100a, 100b, 101, 102, 103 Solid material
110, 130 Edible film
120 Film formulation

The invention claimed is:

1. A method of producing an edible film having a predetermined film shape, the method comprising:
   disposing a surface of a pressing plate along a cutting edge so as to configure a clearance between the cutting edge and the pressing plate;
   kneading edible powder formed of particles smaller than a film thickness, a predetermined component, and an edible liquid having a mass 35% or less of a mass of the powder in a vacuum clay kneader to generate a plastic solid material containing the edible liquid;
   extruding the plastic solid material through a multi-zone extrusion process involving a first zone for carrying and dividing the plastic solid material, a second zone with reduced air pressure for deaerating the plastic solid material, and a third zone for pushing the deaerated plastic solid material into a mold through a cooling jacket with a passage cross-sectional surface that decreases in size towards the mold, thereby applying pressure to the plastic solid material and imparting a predetermined cross-sectional shape to the plastic solid material; and
   slicing the plastic solid material having the predetermined cross-sectional shape with the cutting edge;
   passing the sliced plastic solid material through the clearance between the cutting edge and the pressing plate, so as to deform the sliced plastic solid material into the predetermined film shape having a predetermined thickness, wherein
   the predetermined cross-sectional shape is not the predetermined film shape.

2. The method according to claim 1, wherein the predetermined thickness is greater than or equal to 0.1 mm and less than or equal to 0.5 mm.

3. The method according to claim 1, further comprising adjusting a temperature of the plastic solid material sliced with the cutting edge.

4. The method according to claim 1, wherein
   the predetermined cross-sectional shape is an annular shape, and
   the predetermined film shape is an annular shape.

5. The method according to claim 1, wherein the plastic solid material includes a first solid material and a second solid material in which at least one of the edible powders, the predetermined components, and the edible liquids of the first and second solid materials are different from one another, the method further comprising:
   simultaneously extruding the first and second solid materials from the mold such that the first solid material is present in a first region and the second solid material is present in a second region are formed in the predetermined cross-sectional shape; and
   slicing the solid material by the cutting edge so that the first region where the first solid material is present and the second region where the second solid material is present are separated in the predetermined film shape.

6. The method according to claim 1, further comprising adjusting a temperature of the plastic solid material sliced with the cutting edge so as to regulate the deformation of the plastic solid material into the predetermined film shape.

7. The method according to claim 1, wherein the surface of the pressing plate has fine irregularities.

8. The method according to claim 1, wherein the pressing plate comprises a fluorine resin.

9. The method according to claim 1, wherein the clearance is thicker than the predetermined thickness of the predetermined film shape.

10. The method according to claim 9, wherein the clearance is twice or less than the predetermined thickness of the predetermined film shape.

* * * * *